United States Patent
Sumanaweera et al.

(10) Patent No.: US 7,744,538 B2
(45) Date of Patent: Jun. 29, 2010

(54) MINIMUM ARC VELOCITY INTERPOLATION FOR THREE-DIMENSIONAL ULTRASOUND IMAGING

(75) Inventors: Thilaka S. Sumanaweera, Los Altos, CA (US); Ismayil M. Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1276 days.

(21) Appl. No.: 10/979,584

(22) Filed: Nov. 1, 2004

(65) Prior Publication Data

US 2006/0094963 A1    May 4, 2006

(51) Int. Cl.
*A61B 8/00*    (2006.01)

(52) U.S. Cl. .......................... 600/455; 128/916; 600/443
(58) Field of Classification Search ................. 600/455, 600/456
See application file for complete search history.

(56) References Cited

U.S. PATENT DOCUMENTS

| | | | | |
|---|---|---|---|---|
| 5,425,365 A | * | 6/1995 | Iinuma | 600/455 |
| 5,429,137 A | | 7/1995 | Phelps et al. | |
| 5,724,974 A | * | 3/1998 | Goodsell et al. | 600/453 |
| 5,860,925 A | * | 1/1999 | Liu | 600/443 |
| 6,075,386 A | * | 6/2000 | Naffziger | 326/98 |
| 6,256,039 B1 | * | 7/2001 | Krishnamurthy | 345/420 |
| 7,037,263 B2 | | 5/2006 | Sumanaweera et al. | |
| 7,119,810 B2 | | 10/2006 | Sumaneweear et al. | |
| 2004/0181151 A1 | | 9/2004 | Sumanaweera et al. | |

* cited by examiner

*Primary Examiner*—Eric F Winakur
*Assistant Examiner*—Helene Bor

(57) ABSTRACT

Minimum arc interpolation is performed on velocity information distributed in three dimensions. By using complex representations of the velocity information, the interpolation may more accurately represent the angle or velocity for spatial conversion. Tri-linearly interpolating velocity information converts the information representing a three-dimensional volume to a reconstruction grid. The interpolation is performed with a graphics processing unit. Complex representations of the velocity are loaded as texture data. The graphics processing unit interpolates the data as texture fields. Look-up tables are used to determine an angle from the interpolated complex representation and/or a color value for displaying velocities associated with different spatial locations.

41 Claims, 5 Drawing Sheets

TRILINEAR INTERPOLATION:
FILTERED VELOCITY POINT, $V_{FILTERED}$ 2nd
EIGHT NEIGHBORING VALVES

SIGN ASSIGNMENT LOOK-UP TABLE $V_K[7:0]$ 8 BIT SIGNED VELOCITY VALVE $A_K = V_K[7:6]$ 2 BIT QUADRANT INDICATOR 0,1,2,3

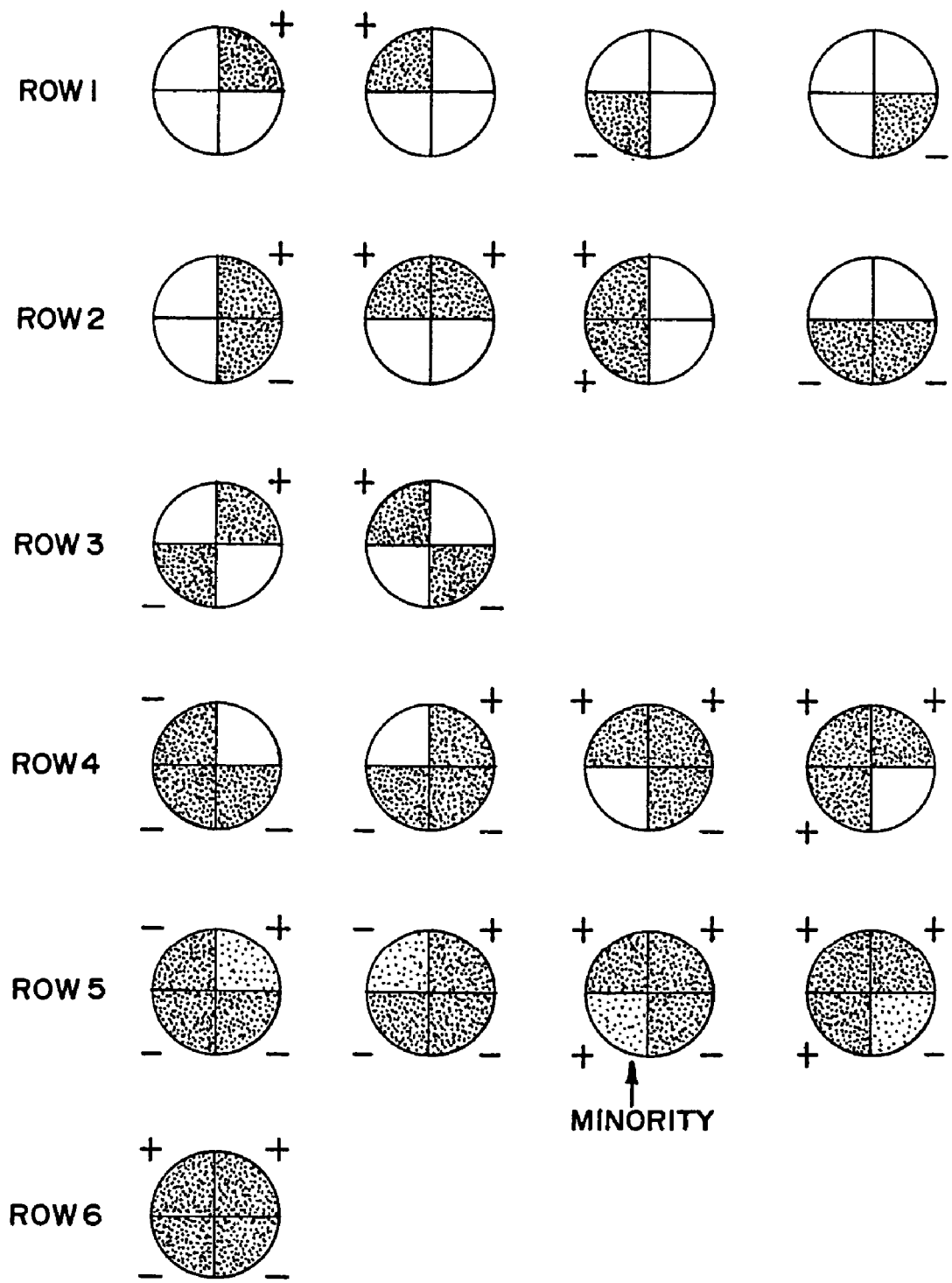
FIG.6 SIGN ASSIGNMENT SCHEME

MINIMUM ARC VELOCITY INTERPOLATION FOR THREE-DIMENSIONAL ULTRASOUND IMAGING

BACKGROUND

The present embodiments relate to interpolation for ultrasound imaging. In particular, velocity information is interpolated for multi-dimensional ultrasound imaging.

In diagnostic medical ultrasound imaging, velocities are estimated for spatial locations within a scan region. The region may be scanned using a polar coordinate format. The display format is frequently different than the scan format. To convert the scan data to data for display, the estimated velocities in the scan format are interpolated to provide estimated velocities in a display format.

Estimated velocities are typically provided as angular measurements. The angle is the phase of the first sample or first order coefficient of an autocorrelation function of echoes returned from a spatial location. The phase angle takes a value between $\pi$ and $-\pi$ in a unit circle. Any interpolation of a phase value accounts for the angular nature of the measurement or introduces undesired artifacts or errors. For example, a linear interpolation may result in an incorrect angle or phase determination. Angular position around the unit circle may be more accurately determined using a minimum arc interpolation. U.S. Pat. No. 5,429,137, the disclosure of which is incorporated herein by references, uses a minimum arc interpolation for two-dimensional scan conversion.

For display, velocity information is mapped to different colors. The hue of a color represents the direction and brightness or shade represents the magnitude of velocity. RGB or other color representations may be interpolated. However, interpolation of colors may produce colors outside of the velocity color map, resulting in user confusion.

BRIEF SUMMARY

By way of introduction, the preferred embodiments described below include methods and systems for interpolating velocity information in ultrasound imaging. Minimum arc interpolation is performed on velocity information distributed in three dimensions. By using complex representations of the velocity information, the interpolation may more accurately represent the angle or velocity for spatial conversion. Tri-linearly interpolating velocity information converts the information representing a scanned three-dimensional volume to a reconstruction grid. The converted information is used for rendering a representation of the three-dimensional volume and/or rendering a two-dimensional image from any arbitrarily selected plane through the volume.

In one embodiment, the interpolation is performed with a graphics processing unit. Complex representations of the velocity are loaded as texture data. The graphics processing unit interpolates the data as texture fields. Look-up tables are used to determine an angle from the interpolated complex representation and/or a color value for displaying velocities associated with different spatial locations.

In a first aspect, a method is provided for interpolating velocity information in ultrasound imaging. Velocity information representing locations distributed along three dimensions is interpolated as a function of a minimum arc. An image is generated from the interpolated velocity information.

In a second aspect, a method is provided for interpolating velocity information in ultrasound imaging. Complex values representing velocity information are interpolated in three dimensions. An image is generated from the interpolated velocity information.

In a third aspect, a system is provided for interpolating velocity information in ultrasound imaging. A velocity estimator is operable to output velocity information representing spatial locations distributed in three dimensions. A graphics processing unit is operable to receive the velocity information, to tri-linearly interpolate the velocity information and to output interpolated data as a function of the interpolated velocity information.

The present invention is defined by the following claims, and nothing in this section should be taken as a limitation on those claims. Further aspects and advantages of the invention are discussed below in conjunction with the preferred embodiments and may be later claimed in combination with or independent of any other aspects or advantages.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 6 is a graphical representation of one embodiment of a sign assignment scheme.

DETAILED DESCRIPTION OF THE DRAWINGS AND PRESENTLY PREFERRED EMBODIMENTS

Ultrasound velocities, such as Doppler velocities, are interpolated for three-dimensional reconstruction or format conversion. A graphics processing unit or accelerator hardware may be used to perform the three-dimensional spatial operations of the velocity information, such as interpolating from velocity information in a complex representation stored as texture data. Any spatial phase processing using a graphics processing unit, including phase or magnitude and phase information may be used. Complex representations of velocity values are interpolated as a function of the minimum arc to avoid artifacts or errors for high velocity, turbulent flow regions.

Figure 1:
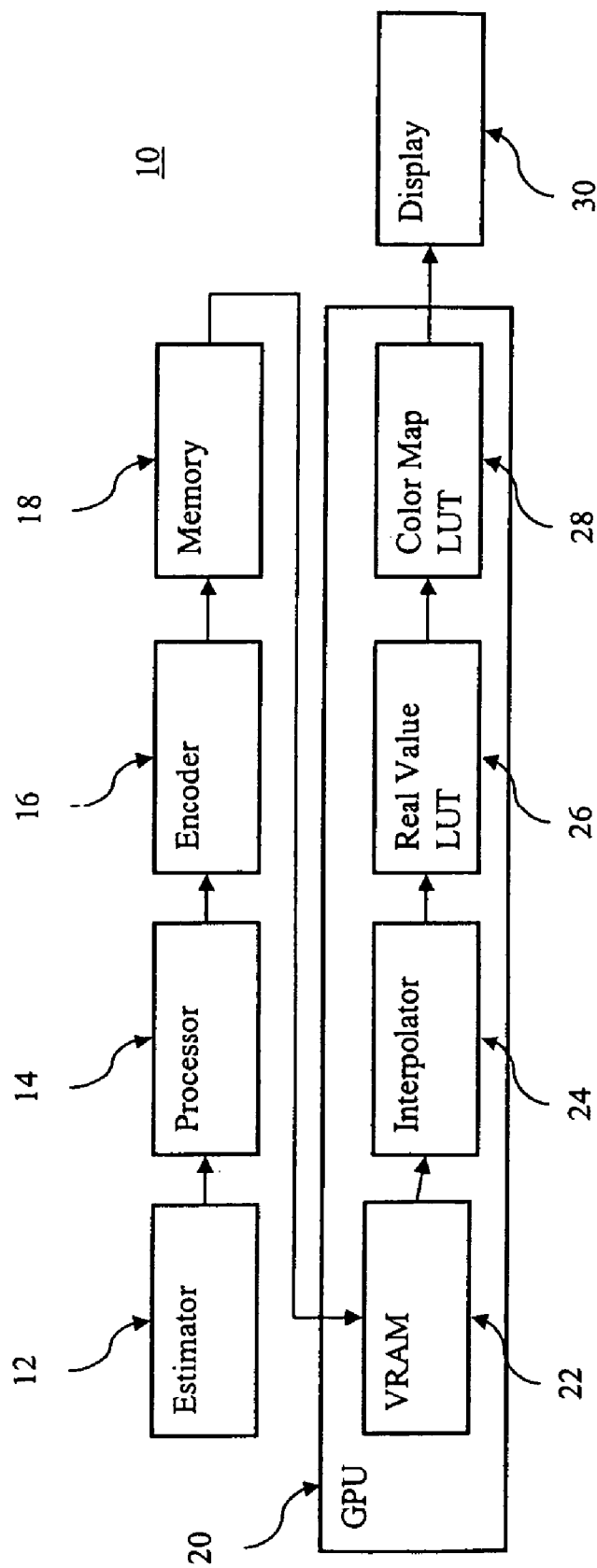
FIG. 1 is a block diagram of one embodiment of a system for interpolating velocity information.

FIG. 1 shows one embodiment of a system 10 for interpolating velocity information in ultrasound imaging. The system includes a velocity estimator 12, a processor 14, an encoder 16, a memory 18, a graphics processing unit 20 and a display 30. Additional, different or fewer components may be provided. For example, the processor 14 is skipped or also implements the encoding of the encoder 16. As another example, the encoder 16 is unneeded as the estimation processor 12 outputs complex representations. In one embodiment, the system 10 is part of a medical diagnostic ultrasound imaging system including transmit and receive beamformers. In alternative embodiments, the system 10 or portions of the system 10 are on a workstation or personal computer.

Ultrasound data reflected from different spatial locations are input to the velocity estimator 12. Using a one-dimensional, two-dimensional, multidimensional or other array, a volume is electronically, mechanically or both electronically and mechanically scanned with ultrasound energy. By scanning a three-dimensional volume, data representing spatial locations distributed in three dimensions, such as two or more samples distributed along each of the three dimensions, is provided. For estimating velocity information, multiple samples from the same or similar spatial locations are sequentially acquired.

The velocity estimator 12 is a flow detector, such as a processor, digital signal processor, analog circuit, digital circuit, application specific integrated circuit, field programmable gate array, combinations thereof, or other structure for determining velocity. In one embodiment, the velocity estimator 12 is a Doppler estimator operable to perform autocorrelation on received information. The velocity estimator 12 outputs an angle or the phase of the first sample of the autocorrelation function for each spatial location. As an alternative to outputting a real value, the velocity may be output as a complex representation, such as in-phase and quadrature values. The velocity estimator 12 may additionally output energy and/or variance information.

The processor 14 alters detected information. For example, the processor 14 is a filter, digital logic, or other device for performing spatial filtering, thresholding and/or persistence processing. Alternatively, the processor 14 is skipped, outputs the data without any processing, or is not provided.

The encoder 16 is a processor, application specific integrated circuit, digital signal processor, field programmable gate array, analog circuit, digital circuit, combinations thereof or other device for converting real values representing velocity into complex representations. Velocity values as used herein include a velocity (distance as a function of time), a phase, a frequency shift, an angle or other value representing velocity. These terms may be used interchangeably herein. The encoder 16 applies the cosine and sine to the input velocity angle. The resulting values are in-phase and quadrature values representing the velocity. In alternative embodiments, the velocity estimator 12 outputs the velocities as complex representations, such as by incorporating the encoder 16 or the processing of the encoder 16 within the velocity estimator 12.

The memory 18 is a buffer, first-in-first-out device, random access memory, cache memory, combinations thereof or other device for storing data to be accessed by the graphics processing unit 20. For example the memory 18 is a RAM of an AGP system. In alternative embodiments, the data is provided directly to the graphics processing unit without previous storage in the memory 18.

The graphics processing unit (GPU) 14 is a processor, digital circuit, analog circuit, application specific integrated circuit, digital signal processor, video card, field programmable gate array, combinations thereof or other now known or later developed device for graphics processing. In one embodiment, the GPU 20 is a graphics processor or video card from nVIDIA, ATI or 3Dlabs. These or other devices using an API of Open GL, DirectX, GDI, GDI+, or other now known or later developed APIs may be used. In one embodiment, the GPU 20 includes a vertex processor, assembly processor, fragment processor, rasterization and interpolation circuits, memories and one or more frame buffers as discrete or integrated components. The GPU 20 is provided on a mother board or a data board, but may be implemented as a single chip, on a circuit on a card or other layout. In one embodiment, the GPU 20 implements the processes and/or includes the hardware disclosed in U.S. Pat. Nos. 7,119,810, 7,037,263, and 6,852,081 (application Ser. Nos. 10/728,666; 10/644,363; and 10/388,128), the disclosures of which are incorporated herein by reference. The GPU 20 receives velocity information in one format and outputs the velocity information in a different format. For example, velocities in a polar coordinate format are received. The GPU 20 converts the data to a Cartesian coordinate or display format.

As shown in FIG. 1, the GPU 20 includes a video memory 22, an interpolator 24, and two look-up tables or memories 26, 28. Additional, different or fewer components may be provided, such as providing the look-up tables 26 and 28 as a single look-up table.

The video memory 22 is a random access memory, but other now known or later developed memories may be used. The video memory 22 stores any of various amounts of information, such as 64, 128, 256 or other numbers of kilobytes. The video memory is operable to receive the velocity information. The GPU 20 accesses information in the video memory 22 for graphics processing. The graphics processing is performed pursuant to the API run by a general processor of the GPU 20. In one embodiment, the data stored within the video memory 22 is structured as texture data, such as having four defined fields for each spatial location.

The interpolator 24 is a vertex processor, fragment processor, control processor, interpolation processor, combinations thereof, or other components of the GPU 20. For example, scan conversion operations are performed with the vertex processor. The vertex processors reformat data from a polar coordinate system to a Cartesian coordinate system. Scan conversion is implemented by assigning coordinants associated with current data as a function of the new format. A linear interpolation by the rasterization and interpolation processor completes the scan conversion. Non-linear operations for scan conversion may be performed with a fragment processor.

The interpolator 24 is operable to tri-linearly interpolate the velocity information. For example, 8 or more samples associated with the scan format surrounding a location associated with the display format are interpolated to the display format location. Tri-linear interpolation interpolates points to points along edges, the points along the edges to points on surfaces, and the points on the surfaces to a final location in three dimensions. Points or points on edges may be directly interpolated to the final location. In one embodiment, the tri-linear interpolation is performed on the velocity information stored as texture data. The texture fields of the GPU 20 are populated with the velocity information, such as using two fields for in-phase and quadrature information. In-phase and quadrature information may be input as the GL_LUMINANCE_ALPHA texture using the OpenGL API. Other APIs such as DirectX may also be used. Additional fields of the texture for a given spatial location may be populated with other information, such as variance, energy or both variance and energy information. For example, four texture fields are provided for each spatial location. Two texture fields are populated with in-phase and quadrature information and the other two texture fields are populated with variance and energy information. The fragment shader of the GPU 20 implements a script for processing the velocity information stored as texture data.

Consider two complex values with unit magnitude, $C_1$ at a point $p_1$ and $C_2$ at a point $p_2$. To find the complex value at a point p on the line joining $p_1$ and $p_2$, the new complex value can be linearly interpolated using minimum arc interpolation. $C_1$ and $C_2$ lie on the unit circle. Minimum arc interpolation first finds the shortest arc between the two complex numbers along the unit circle. It then linearly interpolates the two complex numbers along the minimum arc to find the new complex number. The interpolation can be done on the phase of the complex numbers or on the in-phase (real) and quadrature phases (imaginary) parts of the complex number, followed by re-normalization. Using minimum arc interpolation avoids artifacts associated with the linear interpolation, such as those which occur when interpolating a complex number with a phase equal to negative π and another complex number with a phase equal to positive π at the half way point to a complex number with a zero phase.

Figure 3:
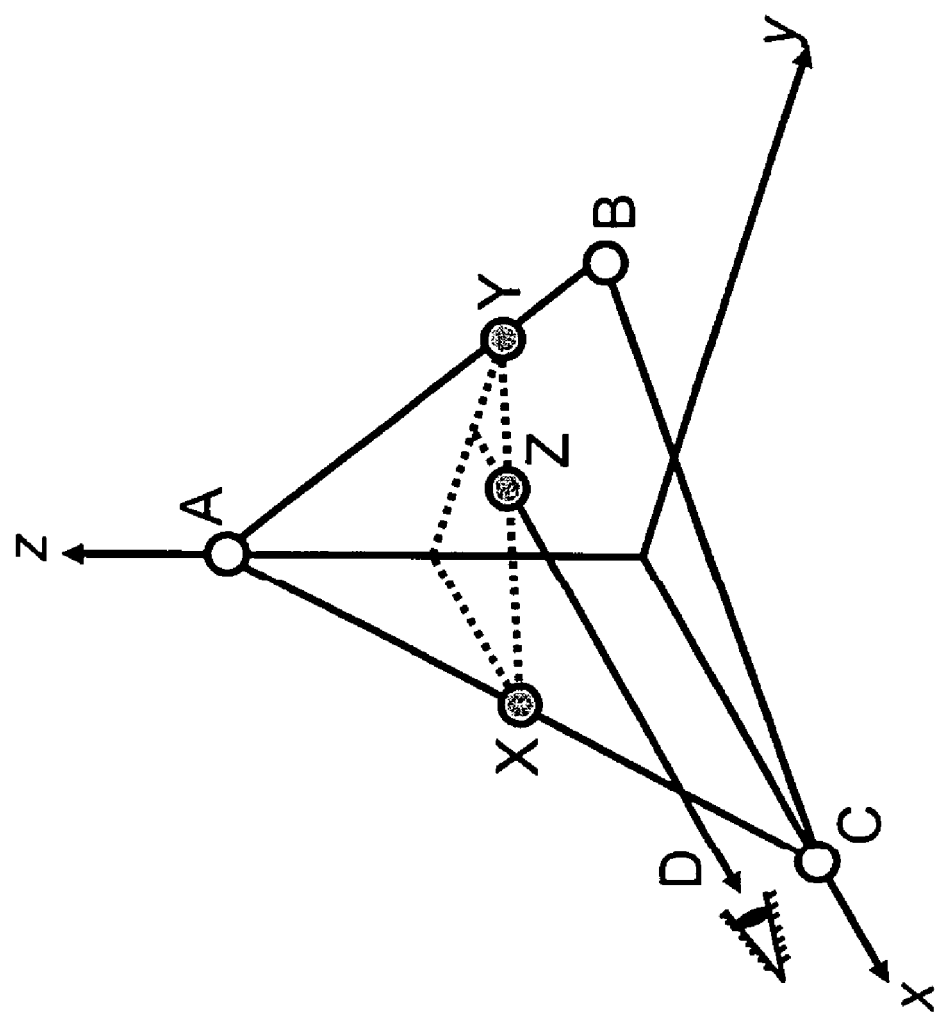
FIG. 3 is a graphical representation of minimum arc interpolation.

The interpolation in three dimensions of velocity information is performed as a function of the minimum arc. Interpolation in three dimensions can be performed by carrying out a series of one dimensional interpolations, with each one dimensional interpolation performed using the minimum arc. FIG. 3 shows an example. Consider a 3D triangle ABC with the corners, A on the z-axis, B on the zy-plane, and C on the x-axis. Assume that there are three values specified for the corners, A, B and C. This triangle is projected using orthographic projection on to a computer screen parallel to the zy-plane, with y being the horizontal axis of the screen. In other words, the triangle is viewed along the line DZ, which is parallel to the x-axis. The line DZ intersects the triangle at Z. The goal is to compute the value at the point Z using interpolation. To do this, the coordinates for X and Y, two points on the sides AC and AB, respectively, are computed such that line XY is parallel to the xy-plane. Following this, the value at X is first computed by interpolating the values at A and C along the minimum-arc. The value at Y is then computed by interpolating the values at A and B along the minimum-arc. Finally, the value at Z is computed by interpolating the values at X and Y along the minimum arc. Other types of interpolation schemes can also be used.

Figure 4:
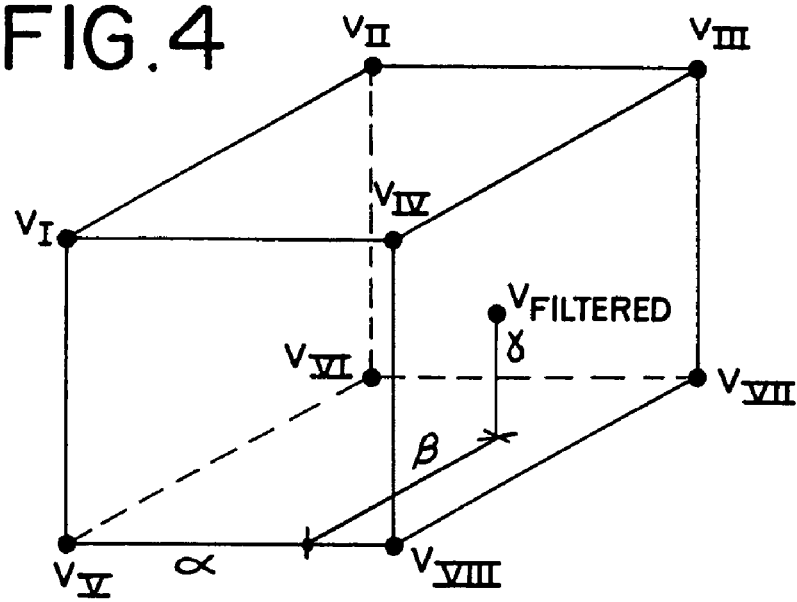
FIG. 4 is a graphical representation of an embodiment of a spatial relationship for interpolation.

In an alternative embodiment for tri-linear interpolation as a function of a minimum arc, a position based approximation is used. Tri-linear interpolation operations combine or filter values from eight neighboring points to determine a velocity value, $V_{filtered}$. By appropriately assigning a sign correction to each of the eight velocities, the correct (or most likely) interpolation path can be taken. Eight neighboring velocity values in three dimensional space, $V_I$ thru $V_{VIII}$ are shown in FIG. 4. The parameters α, β and γ range from 0 to 1.0 and indicate the relative spatial location of $V_{filtered}$ within the prism formed by the eight neighboring points.

Figure 5:
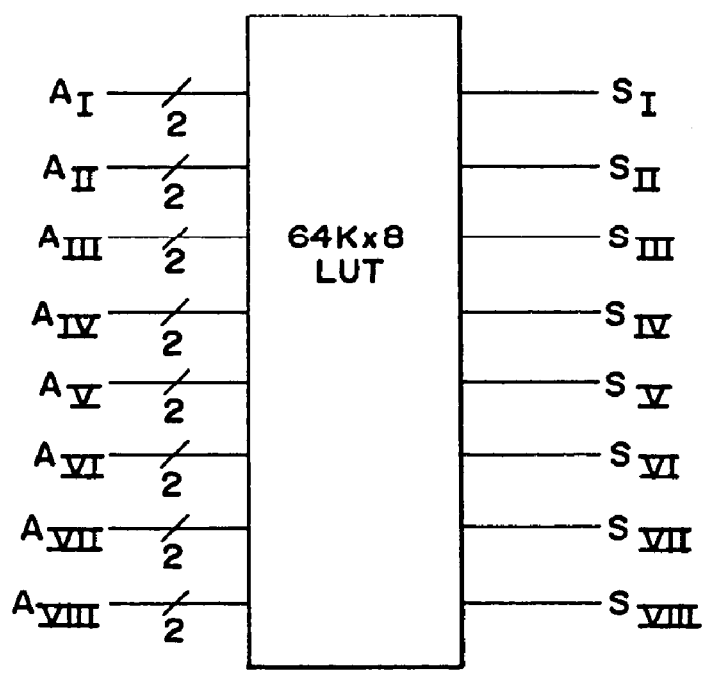
FIG. 5 is a block diagram of one embodiment of a look-up table.

A sign correction for each velocity $V_k$ is determined by a lookup table shown in FIG. 5. The upper two bits of each velocity is applied to the LUT so that the quadrant of each velocity input is known. The contents of the LUT are then set to choose the correction sign for each of the inputs. The sign is set according to a "majority rule" minimum arc path algorithm, graphically depicted in FIG. 6.

If all eight inputs fall within a single quadrant then the sign correction bit for each velocity value is set to the same value according to which quadrant (shown shaded) in the first row of FIG. 6, unchanged from their original signs.

If all eight inputs fall within two adjacent quadrants then they are set according to the graphic in the second row of FIG. 6, with the sign values unchanged from their original value except in the case where velocity values fall in the $2^{nd}$ and $3^{rd}$ quadrants. In this case the values in the $3^{rd}$ quadrant values are treated as positive rather than negative velocities.

If velocity values fall in opposite quadrants, then the original sign values are used. The third row of FIG. 6 shows this circumstance.

If values fall in three quadrants, then the signs are assigned according to the fourth row of FIG. 6. The signs are adjusted from the original values when velocities again cross the $2^{nd}$ and $3^{rd}$ quadrants.

If velocity values fall in all four quadrants, then the sign assignment rule is set by looking at the quadrant with the minority of velocity values. Signs are assigned to all velocity values according to the fifth row of FIG. 6 based on the quadrant with the least number of velocity values. If there are two velocity values in each quadrant, then the velocity values are unchanged, as shown in row 6.

Alternative sign assignment rules can be used. Which quadrants have the larger number of velocity values may be considered in assigning the correction signs. Additional numbers of bits can be input to the LUTs to determine the most likely interpolation path so that the unit circle is divided into octants. In the case of octants, three bits of octant indicators are input to the LUT for each of the eight velocity values. Since this would lead to a very large LUT (16 Mbytes), the majority rule operations may be performed with counters and logic or broken up into a series of calculations. A large number of permutations are possible. The sign bits of each of the velocity values are considered for adjustment prior to the final linear combination operation based on the most likely interpolation path.

The sign correction is applied to each velocity by appending the single bit LUT sign correction value Si for each velocity value, $V_k$.

$Vcorr_k=[S_k][V_k[7:1]]$ 8-bit sign corrected velocity value

Other numbers of bits may be used. The tri-linearly interpolated filtered velocity is computed from the corrected velocities and spatially dependent weights according to the following formula:

$$V_{filtered} = Vcorr_I(1-\alpha)(1-\beta)(\gamma) + \\ Vcorr_{II}(1-\alpha)(\beta)(\gamma) + Vcorr_{III}(\alpha)(\beta)(\gamma) + Vcorr_{IV}(\alpha)(1-\beta)(\gamma) + \\ Vcorr_V(1-\alpha)(1-\beta)(1-\gamma) + Vcorr_{VI}(1-\alpha)(\beta)(1-\gamma) + \\ Vcorr_{VII}(\alpha)(\beta)(1-\gamma) + Vcorr_{VIII}(\alpha)(1-\beta)(1-\gamma)$$

The eight bits to the left of the radix point are retained in the final output, discarding upper "overflow" bits, placing the resulting filtered velocity in the range −128 to +127.

In yet another example, a series of 1D interpolations using the 8 neighbors of a given point is used, where the 8 neighbors are the corners of the cube containing the given point in the original data grid. In yet another example, a series of 1D interpolations using the 4 neighbors of a given point are used, where the 4 neighbors are the corners of the tetrahedron containing the given point in the original data grid.

The look-up table 26 is a memory, buffer, texture look-up table or other now known or later developed structure for determining a real value for the velocity from a complex representation. The interpolated in-phase and quadrature information for each spatial location in the reconstructed or output format is input to the look-up table 26. The associated output corresponds to a real value, such as a velocity, angle, or phase represented by the complex input. For example, the look-up table 26 implements an arctan2 function (e.g. φ=Arctan2(I,Q)). In alternative embodiments, any processor or other device calculates the real values from the complex representations with the arctan2 function. Other functions may be used or implemented, such as the arctangent function for non-directional velocities.

The color map look-up table 28 is a texture look-up table, such as a memory, buffer or other now known or later developed device for implementing a look-up table. Alternatively, the look-up table 28 is implemented as a processor or other device operable to calculate color values from velocity information. The color map look-up table 28 implements one or more color maps that are linear or non-linear functions of the input velocity. A given color map is selected by the user or is applied for a specific application. The color mapping function may be represented mathematically as:

$$c=F(\phi)$$

where $\phi$ is the angle or other velocity information and c is a color value, such as an RGB, RGB and alpha, YUV or other color representation. The argument of the function F, $\phi$, is limited by $\pi$ and $-\pi$. The color map look-up table 28 is operable to convert the interpolated data into color information.

Where a baseline shift is desired, such as in response to a user input or adjustment, a different color map is loaded into the color map look-up table 28. The GPU 20 shifts the base line of the velocity scale for the interpolated data as a function of the color map of the look-up table 28.

In an alternative embodiment, the real value look-up table 26 and color map look-up table 28 are combined into a single look-up table. The interpolated in-phase and quadrature information is input to a single look-up table and a color value is output. Mathematically, a single look-up table is represented as:

$$c=F(\text{Arc tan }2(I,Q))$$

In one embodiment, one texture addressing unit or texture data table stores the input velocity in-phase and quadrature information. Where four fields are provided and only velocity information is input, two extra fields may be populated, unpopulated, populated with in-phase information, populated with quadrature information or otherwise ignored. Another texture addressing unit or texture data table stores a combined look-up table for determining output color in response to interpolated, complex representations of velocity. Other texture addressing units or data tables may be used for other purposes, such as providing Cartesian-to-acoustic transformations for scalpel operations, calculations or other processes to determine information from data in an acoustic format.

The output color information is provided for further processing or calculations in one embodiment. Alternatively or additionally, the GPU 20 renders a representation of the three-dimensional volume from the interpolated data either before conversion to a real value, after conversion to real values, before conversion to color information or after conversion to color information. Any three-dimensional rendering techniques may be used, such as maximum, minimum, weighted or alpha blended intensity projections. A two-dimensional representation of the three-dimensional volume from a given viewing direction is rendered. Alternatively or additionally, the GPU 20 is operable to render a planar reconstruction of the interpolated data. The planar reconstruction corresponds to a plane different than or the same as any of the scan planes used to acquire velocity information. Any arbitrary plane may be selected through the three-dimensional volume represented by the interpolated or reconstructed data. The data along the plane is then used to generate a two-dimensional image.

The GPU 20 may render an image in response to interpolated velocity information as well as interpolated variance and/or energy information. Variance and energy may be linearly interpolated, such as without conversion to complex representations. The energy and/or variance information may be used for rendering. For example, energy is used as an opacity weighting for blending and volume rendering the velocity information. As another example, energy and/or variance are used to threshold the velocity information for inclusion or exclusion from the rendering process.

The display 30 is operable to display an ultrasound image as a function of the output interpolated data. For example, the display 30 displays a rendered image representing a volume, a planar reconstruction, or other ultrasound image responsive to the interpolated data. The displayed image is generated by the GPU 20 or another device from the interpolated data.

Figure 2:
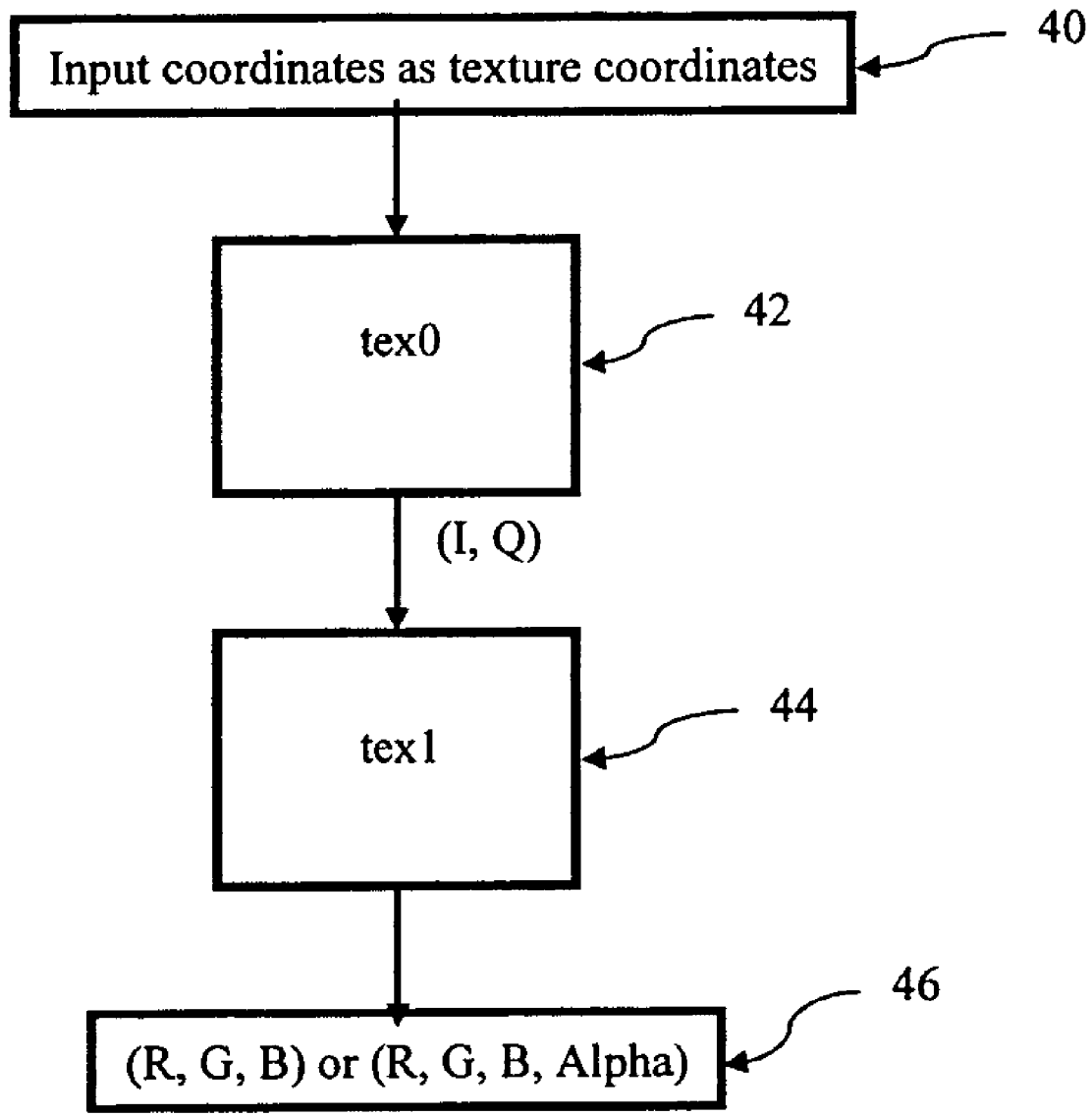
FIG. 2 is a flowchart diagram of one embodiment of a method for interpolating velocity information.

FIG. 2 shows one embodiment of a method for interpolating velocity information in ultrasound imaging. The method is implemented using the system 10 of FIG. 1 or a different system. As shown, the method of FIG. 2 uses texture fields of a GPU for interpolating velocity information. In alternative embodiments, non-texture data structures or a different processor than a GPU is used for implementing the method of FIG. 2. Additional, different or fewer acts may be provided than shown in FIG. 2.

In act 40, velocity information associated with different scan coordinants are input as texture information. In one embodiment, complex representations of the velocity information are input, such as in-phase and quadrature information. Alternatively, angle, phase or other velocity information is input and then later converted to a complex representation.

The input velocity information represents coordinates distributed throughout a three-dimensional scan volume, such as data representing a plurality of samples along each of three dimensions relative to the transducer. Alternatively, the input information represents spatial locations distributed along a plane or two-dimensional region.

In act 42, the input velocity information is interpolated. The interpolation is performed as a function of a minimum arc. Tri-linear interpolation of complex values representing velocity information is performed. A value associated with one location is interpolated from in-phase and quadrature components of velocity information at 8 or more adjacent locations to convert from a scan format to a display or Cartesian coordinate format.

A graphics processing unit may perform the interpolation, such as interpolating the velocity information as texture data. Velocity information for each of the plurality of spatial locations is stored as texture data. Using a texture structure, the GPU interpolates in response to a shader or fragment process.

Other information may be interpolated as a function of the minimum arc or using linear interpolation. For example, variance, energy or both variance and energy are tri-linearly interpolated as texture data by the graphics processing unit using a linear interpolation technique. Different fields of texture data are interpolated differently. Alternatively, linear interpolation is performed between two spatial locations for each of the fields. Since the velocity information is represented as complex values associated with two different fields, a minimum arc interpolation is performed based on the component or real and imaginary linear interpolations. Linear interpolation without minimal arc interpolation may be provided for variance or energy information.

The interpolation is performed with or without weighted values. For example, data associated with a spatial location closer to an output spatial location than other data is more heavily weighted. For velocity information, the output of act 42 is an interpolated complex representation of velocity.

In act 44, velocity information is determined from the complex representation. A texture or other data structure is used for implementing a look-up table to convert from the complex representations to real values, convert from complex representations to color values, and/or convert from real values to color values. Separate look-up tables or processes are provided for different conversions or determinations. Alternatively, a common look-up table is provided for converting complex representation into a real value and determining a color value for real value.

A look-up table or process is used to determine a real interpolated velocity value from the interpolated complex representation. An arctan2 function is used to calculate to the real values from the interpolated complex representations. The calculation is performed using a look-up table or a process.

The interpolated velocity information is converted into color information. A look-up table or other process is used to convert the velocity information to a desired color or range of colors, such as associated with a velocity color map. The velocity color map may include directional information or non-directional information. Any of shade, color, hue, brightness or other characteristics are used to distinguish one velocity from another. Different color maps may be used for different purposes, such as selecting a color map based on a desired amount of baseline shift of a velocity scale.

In act 46, the output interpolated velocity information is used to generate an image. RGB or RGB and alpha values are used for generating a color image, but a black and white image may alternatively be generated. A representation of a three-dimensional volume is rendered from the interpolated velocity information for three-dimensional imaging. A planar reconstruction is rendered from the interpolated velocity information for two-dimensional imaging of the three-dimensional volume. The planar reconstruction corresponds to a display plane that is different than or the same as the scan plane used to acquire velocity information. The image is rendered using the graphics processing unit or another device.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for interpolating velocity information in ultrasound imaging, the method comprising:
   (a) obtaining velocity information, the velocity information comprising velocities representing amount of motion per unit of time at locations distributed in a grid throughout a volume, the locations along three-dimensions;
   (b) interpolating, by a processor, the velocities as a function of a minimum arc along a unit circle; and
   (c) generating an image from the interpolated velocity information.

2. The method of claim 1 wherein (b) comprises interpolating with a graphics processing unit.

3. The method of claim 2 wherein (b) comprises interpolating the velocity information as texture data of the graphics processing unit.

4. The method of claim 3 further comprising:
   (d) including variance, energy or both variance and energy as texture data of the graphics processing unit, the texture data having first and second fields for complex representation of the velocity information and having at least a third field for variance or energy;
   wherein (c) comprises generating the image as a function of variance or energy.

5. The method of claim 2 wherein (b) comprises performing tri-linear interpolation of complex representations of velocity;
   further comprising:
   (d) determining a real interpolated velocity value from the interpolated complex representation with a look-up table of the graphic processing unit.

6. The method of claim 2 wherein (b) comprises performing tri-linear interpolation of complex representations of velocity;
   further comprising:
   (d) converting the interpolated velocity information into color information.

7. The method of claim 2 wherein (c) comprises generating the image with the graphics processing unit.

8. The method of claim 1 wherein (b) comprises performing tri-linear interpolation of complex representations of velocity.

9. The method of claim 8 further comprising:
   (d) determining a real interpolated velocity value from the interpolated complex representation.

10. The method of claim 9 wherein (d) comprises calculating an arc tan 2 function of the interpolated complex representation.

11. The method of claim 1 further comprising:
   (d) converting the interpolated velocity information into color information;
   wherein (c) comprises generating a color image.

12. The method of claim 11 wherein (d) comprises inputting the interpolated velocity information into a look-up table:
   further comprising:
   (e) shifting a baseline of a velocity scale for the interpolated velocity information as a function of a color map of the look-up table.

13. The method of claim 1 wherein (c) comprises rendering a representation of a three-dimensional volume from the interpolated velocity information.

14. The method of claim 1 wherein (c) comprises rendering a planar reconstruction from the interpolated velocity information, the planar reconstruction corresponding to a first plane different than any scan plane used to acquire the velocity information.

15. The method of claim 1 wherein (b) comprises interpolating from velocity information representing four locations.

16. The method of claim 1 wherein (b) comprises:
   (b1) altering a sign value as a function of a velocity for velocity information associated with at least one location; and
   (b2) interpolating with the altered sign value of the velocity.

17. The method of claim 16 wherein (b1) comprises altering sign values of velocities as a function of quadrant.

18. A method for interpolating velocity information in ultrasound imaging, the method comprising:
   (a) obtaining complex values representing velocities corresponding to an amount of motion per unit of time, the complex values comprising in-phase and quadrature components;

(b) interpolating, in three dimensions by a processor, the complex values; and (c) generating an image from the interpolated velocity information.

19. The method of claim 18 wherein (b) comprises interpolating with a graphics processing unit.

20. The method of claim 19 wherein (b) comprises interpolating the velocity information as texture data of the graphics processing unit.

21. The method of claim 20 further comprising:

(d) including variance, energy or both variance and energy as texture data of the graphics processing unit, the texture data having first and second fields for each complex value of the velocities and having at least a third field for variance or energy;

wherein (c) comprises generating the image as a function of variance or energy.

22. The method of claim 18 wherein (b) comprises determining a value at a first location with tri-linear interpolation of the in-phase and quadrature components for velocities at eight or more locations adjacent to the first location.

23. The method of claim 18 further comprising:

(d) determining a real interpolated velocity value from the interpolated velocity information.

24. The method of claim 18 further comprising:

(d) converting the interpolated velocity information into color information with a look-up table;

(e) shifting a baseline of a velocity scale for the interpolated velocity information as a function of a color map of the look-up table wherein (c) comprises generating a color image.

25. The method of claim 18 wherein (b) comprises interpolating a value from velocity information representing four locations.

26. The method of claim 18 wherein (b) comprises:

(b1) assigning a sign correction to the complex values; and
(b2) interpolating the complex values with the assigned sign corrections.

27. The method of claim 26 wherein (b1) comprises assigning sign values as a function of quadrant.

28. A system for interpolating velocity information in ultrasound imaging, the system comprising:

a velocity estimator operable to output velocity information representing spatial locations distributed in three-dimensions; and a graphic processing unit operable to receive the velocity information, to tri-linearly interpolate the velocity information, the tri-linear interpolation comprising interpolating, for a each one of the spatial locations, from other spatial locations along edges to edge locations, edge locations to surface locations, and surface locations to the one spatial location, the edge locations and surface locations being within a neighborhood around the one spatial location, and to output interpolated data as a function of the interpolated velocity information.

29. The system of claim 28 wherein the graphic processing unit is operable to tri-linearly interpolate the velocity information as a function of a minimum arc.

30. The system of claim 28 wherein the graphic processing unit is operable to tri-linearly interpolate the velocity information, the velocity information being complex representations.

31. The system of claim 28 wherein the graphics processing unit is operable to tri-linearly interpolate the velocity information as texture data.

32. The system of claim 31 wherein texture fields of the graphics processing unit are populated with (a) the velocity information and (b) variance, energy or both variance and energy information.

33. The system of claim 28 wherein the velocity estimator is operable to output the velocity information as angles;

further comprising:

an encoder operable to determine complex representations of the velocity information;

wherein the graphics processing unit is operable to tri-linearly interpolate the complex representations and operable to determine real values from the interpolated data.

34. The system of claim 33 wherein the graphics processing unit is operable to determine the real values by applying an arc tan 2 function of the interpolated data with a look-up table.

35. The system of claim 28 wherein the graphics processing unit is operable to convert the interpolated data into color information.

36. The system of claim 35 wherein the graphics processing unit is operable to convert with a look-up table and is operable to shift a baseline of a velocity scale for the interpolated data as a function of a color map of the look-up table.

37. The system of claim 28 wherein the graphics processing unit is operable to render a representation of a three-dimensional volume from the interpolated data.

38. The system of claim 28 wherein the graphics processing unit is operable to render a planar reconstruction from the interpolated data, the planar reconstruction corresponding to a first plane different than any scan plane used to acquire the velocity information.

39. The system of claim 28 wherein the graphics processing unit is operable to determine real values by applying an arc tan 2 function of the interpolated velocity information with a look-up table.

40. A system for interpolating velocity information in ultrasound imaging, the system comprising:

a velocity estimator operable to output velocities representing an amount of motion per unit of time at spatial locations distributed in at least two-dimensions; and a graphic processing unit operable to receive the velocity values, to tri-linearly interpolate the velocity values as a function of a minimum arc of a unit circle, and to output interpolated data as a function of the interpolated velocity values.

41. The system of claim 40 wherein the graphic processing unit is operable to interpolate the velocity values as texture data, the velocity values being complex representations.

* * * * *